US009550961B2

(12) United States Patent
Negishi et al.

(10) Patent No.: US 9,550,961 B2
(45) Date of Patent: *Jan. 24, 2017

(54) LIPASE POWDER COMPOSITIONS

(75) Inventors: Satoshi Negishi, Yokosuka (JP); Junko Suzuki, Yokosuka (JP); Isamu Takahashi, Yokosuka (JP); Hans Christian Holm, Bagsvaerd (DK)

(73) Assignees: THE NISSHIN OILLIO GROUP, LTD., Tokyo (JP); NOVOZYMES A/S, Bagsvaerd (DK)

( * ) Notice: Subject to any disclaimer, the term of this patent is extended or adjusted under 35 U.S.C. 154(b) by 294 days.

This patent is subject to a terminal disclaimer.

(21) Appl. No.: 12/000,032

(22) Filed: Dec. 7, 2007

(65) Prior Publication Data

US 2008/0102500 A1    May 1, 2008

Related U.S. Application Data

(63) Continuation of application No. PCT/JP2006/311394, filed on Jun. 7, 2006.

(30) Foreign Application Priority Data

Jun. 9, 2005 (JP) .................................. 2005-169836

(51) Int. Cl.
| | | |
|---|---|---|
| C12N 11/12 | (2006.01) | |
| C11C 3/10 | (2006.01) | |
| C12N 9/20 | (2006.01) | |
| C12N 11/14 | (2006.01) | |
| C12P 7/64 | (2006.01) | |

(52) U.S. Cl.
CPC . *C11C 3/10* (2013.01); *C12N 9/20* (2013.01); *C12N 11/14* (2013.01); *C12P 7/6436* (2013.01); *C12P 7/6454* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 5,342,768 A | * | 8/1994 | Pedersen et al. | 435/134 |
| 5,902,738 A | * | 5/1999 | Orsat et al. | 435/155 |
| 6,156,548 A | * | 12/2000 | Christensen et al. | 435/134 |
| 6,372,472 B1 | * | 4/2002 | Nehls et al. | 435/198 |

FOREIGN PATENT DOCUMENTS

| | | |
|---|---|---|
| EP | 0 140 542 A1 | 5/1985 |
| EP | 1 042 458 | 11/2003 |
| JP | 60-98984 A | 6/1985 |
| JP | 61-202688 A | 9/1986 |
| JP | 01-262795 A | 10/1989 |
| JP | 02-138986 A | 5/1990 |
| JP | 03-061485 A | 3/1991 |
| JP | 4-501664 A | 3/1992 |
| JP | 07-079789 A | 3/1995 |
| JP | 2668187 B | 7/1997 |
| JP | 9-508803 A | 9/1997 |
| JP | 2000-106873 A | 4/2000 |
| JP | 2001-178488 A | 7/2001 |
| JP | 2001178488 A * | 7/2001 |
| JP | 2002-500007 | 1/2002 |
| WO | WO 90/05778 A1 | 5/1990 |
| WO | WO 95/22606 A1 | 8/1995 |
| WO | WO 2005/071053 | 8/2005 |

OTHER PUBLICATIONS

Christensen et al. (2003) Eur. J. Lipid Sci. Technol. 105: 318-321.*
International Search Report for PCT/JP2006/311394 dated Sep. 26, 2006 PCT/ISA/210 and Written Opinion PCT/ISA/237.
Office Action from European Application No. 06757101.8, mailed on Dec. 8, 2009.
Taiwanese Office Action mailed on Jan. 12, 2012, in corresponding Taiwanese Patent Application 095120441.
M. Christensen et al., *Industrial lipase immobilization*, 105 Eur. J. Lipid Sci. Technol. 318-321 (2003).

* cited by examiner

*Primary Examiner* — Lisa J Hobbs
(74) *Attorney, Agent, or Firm* — Buchanan, Ingersoll & Rooney PC

(57) ABSTRACT

The present invention provides a lipase powder composition which comprises a filter aid(s) and a product obtained by pulverizing a *Thermomyces* sp.-derived lipase immobilized to a silica carrier(s) into the average particle diameter of 1 μm or more and less than 300 μm. This lipase powder composition improves the lipase activity and operability and, therefore, can be suitably used in the methods for exchanging esters of fats and oils and for esterification.

3 Claims, 1 Drawing Sheet

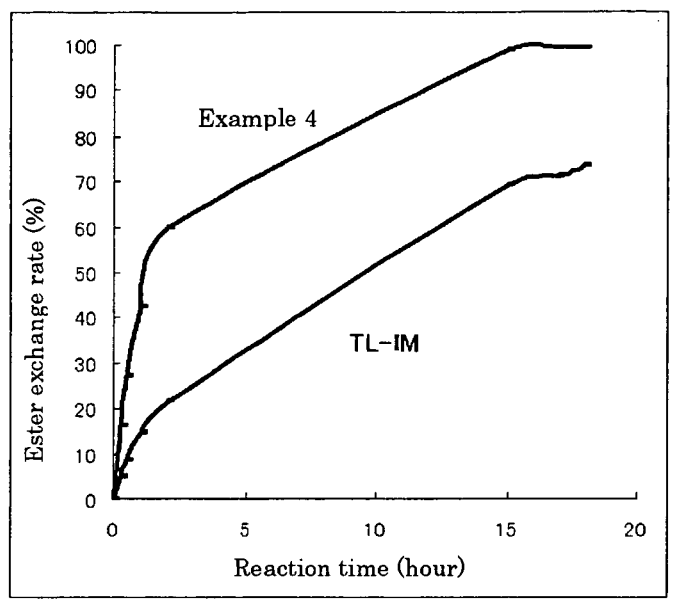

LIPASE POWDER COMPOSITIONS

TECHNICAL FIELD OF THE INVENTION

The present invention relates to lipase powder compositions that can be suitably used in various esterification reactions and ester exchange reactions; and methods for exchanging esters of fats and oils wherein the lipase powder compositions are used.

BACKGROUND OF THE INVENTION

Lipases are widely used in esterification reactions of various carboxylic acids such as a fatty acid with alcohols such as monoalcohol and polyalcohol or ester exchange reactions between several carboxylic esters. Among them, the ester exchange reactions are important technology including modification of fats and oils of animals and plants and as a method for producing esters of various fatty acids, sugar esters and steroids. When lipases that are fat and oil hydrolases are used as a catalyst in those reactions, ester exchange reactions can be conducted under the temperate condition of room temperature to about 70° C. Therefore, use of lipases can not only inhibit side reactions and reduce energy costs as compared with the prior chemical reactions, but also its safety is high because the lipases as the catalyst are natural products. Further, objective compounds can be effectively produced due to its substrate specificity or positional specificity. However, the lipase activity does not sufficiently develop when lipase powder is directly used in ester exchange reactions. In addition to it, it is difficult to equally disperse basically water-soluble lipases in oil-based raw materials and then to collect them. Therefore, conventionally, it is common that lipases are immobilized to some carriers such as anion-exchange resins (Patent Literature 1), phenol adsorption resins (Patent Literature 2), hydrophobic carriers (Patent Literature 3), cation-exchange resins (Patent Literature 4), and chelate resins (Patent Literature 5), and then used in esterifications and ester exchange reactions.

However, since the lipase activity lowers when immobilizing lipases to carriers, various technologies using lipase powder have been developed.

More concretely, the method has been suggested which comprises the steps of dispersing lipase powder in the raw material containing an ester(s) in the presence or absence of an inactive organic solvent(s); and then conducting the ester exchange reaction so that 90% or more of the dispersed lipase powder particles maintain the particle diameter of 1 to 100 μm in the ester exchange reaction (Patent Literature 6). Further, the method has been suggested to use enzymatic powder obtained by drying an enzymatic solution containing a phospholipid(s) and a lipophilic vitamin(s) (Patent Literature 7).

[Patent Literature 1] Japanese Patent Unexamined Publication No. Sho 60-98984
[Patent Literature 2] Japanese Patent Unexamined Publication No. Sho 61-202688
[Patent Literature 3] Japanese Patent Unexamined Publication No. Hei 2-138986
[Patent Literature 4] Japanese Patent Unexamined Publication No. Hei 3-61485
[Patent Literature 5] Japanese Patent Unexamined Publication No. Hei 1-262795
[Patent Literature 6] Japanese Patent No. 2668187
[Patent Literature 7] Japanese Patent Unexamined Publication No. 2000-106873

DISCLOSURE OF THE INVENTION

The object of the present invention is to provide lipase powder compositions of which lipase activity and operability are improved.

The further object of the present invention is to provide methods for exchanging esters of fats and oils wherein the lipase powder compositions are used.

The additional object of the present invention is to provide methods of esterification wherein the lipase powder compositions are used.

The present invention has been completed based on the finding that the above problems can be solved by combining pulverized products of specific immobilized lipases with filter aids.

Namely, the present invention provides a lipase powder composition which comprises a filter aid(s) and a product obtained by pulverizing a *Thermomyces* sp.-derived lipase immobilized to a silica carrier(s) into the average particle diameter of 1 μg m or more and less than 300 μm.

The present invention also provides a method for exchanging esters of fats and oils which comprises the steps of conducting the ester exchange reaction of the fats and oils in the presence of the filter aid(s) and the product obtained by pulverizing a *Thermomyces* sp.-derived lipase immobilized to a silica carrier(s) into the average particle diameter of 1 μm or more and less than 300 μm; then collecting the filter aid(s) and the pulverized product; and recycling them.

The present invention additionally provides a method of esterification which comprises the steps of conducting the esterification reaction in the presence of the filter aid(s) and the product obtained by pulverizing a *Thermomyces* sp.-derived lipase immobilized to a silica carrier(s) into the average particle diameter of 1 μm or more and less than 300 μm; then collecting the filter aid(s) and the pulverized product; and recycling them.

BRIEF DESCRIPTION OF THE DRAWINGS

FIG. 1 shows changes in the ester exchange ratios when using the lipase powder composition of the present invention (Example 4) and the immobilized lipase before pulverizing (Lipozyme TL-IM).

BEST MODE FOR CARRYING OUT THE INVENTION

Lipases used in the present invention are derived from *Thermomyces* sp. and the present invention uses a product obtained by pulverizing the lipases immobilized to a silica carrier(s) into the average particle diameter of 1 μm or more and less than 300 μm. It is preferable that the average particle diameter of the lipases immobilized to a silica carrier(s) is 300 to 1000 μm. These immobilized lipases can be obtained as Lipozyme TL-IM by Novozymes A/S, for example.

It is preferable that such immobilized lipases are pulverized by ordinary grinders into the average particle diameter of 1 μm or more and less than 300 μm, more preferably 1 to 200 μm, further more preferably 1 to 100 μm, and particularly preferably 20 to 100 μm. The grinders include mortars, friction-shear grinders, cutter grinders, millstones (mycolloiders, masscolloiders), coffee mills, power mills, pin mills, impact grinders (hammer mills, ball mills), roll mills and airflow mills, homogenizers, and ultrasonic grinders.

Meanwhile, the filter aids used in the present invention include inorganic filter aids such as Celite and organic filter aids such as fibers e.g. cellulose and pulverized products thereof. The organic filter aids, and especially organic polymeric filter aids are preferable among them. Cellulose is further more preferable among them and is marketed as a trade name: KC Flock by Nippon Paper Chemicals Co., Ltd, for example. It is preferable that the filter aids are powdery and have the average particle diameter of 10 to 90 μm.

The mass ratio of the lipase pulverized product to the filter aid(s) is preferably 1/10 to 10/1 and more preferably 1/7 to 2/1.

The lipase powder compositions of the present invention must contain the lipase pulverized product and the filter aid(s).

The lipase powder compositions of the present invention can be used without change in the ester exchange reactions fats and oils and the esterification reactions. Further, they can also be purified by contacting a long chain fatty acid triglyceride(s) and a medium-chain triglyceride(s) and then collecting them. This method can improve the lipase activity at the same time.

The long chain fatty acid triglycerides used therein are preferably triglycerides having 14 to 24 carbon atoms in a constituent fatty acid. They are particularly preferably vegetable oils selected from the group consisting of canola oil, soybean oil, sunflower oil, safflower oil and corn oil.

The medium-chain triglycerides are preferably triglycerides having 6 to 12 carbon atoms in a constituent fatty acid. Such fatty acid triglycerides can be produced by publicly known methods, or commercially available products thereof can be used. As for the commercially available products, for example, it is marketed as a trade name: ODO by The Nisshin OilliO Group, Ltd.

It is preferable that a long chain fatty acid triglyceride(s) and a medium-chain triglyceride(s) are used in the mass ratio of 95:5 to 50:50. 2 to 100 times mass of triglyceride(s) is preferably contacted to a total mass of the lipase.

As for the esterification reactions wherein the lipase powder compositions of the present invention are used, it is preferable to conduct the esterification reaction by the method comprising the steps of esterifying fats and oils in the presence of the lipase powder compositions; and collecting and recycling the lipase powder compositions.

Further it is also preferable to esterify fats and oils in the presence of a filter aid(s) and a product obtained by pulverizing a *Thermomyces* sp.-derived lipase immobilized to a silica carrier(s) into the particle diameter of 1 μm or more and less than 300 μm; and collect and recycle the filter aid(s) and the pulverized product.

According to the present invention, since the usability (operability) of the lipase powder compositions in esterification reactions and ester exchange reactions are improved together with the improvement in its lipase activity and they can be repeatedly used in these reactions by recycling, the lipase powder compositions of the present invention can be suitably used in modification of fats and oils by the ester exchanges thereof and the like on the industrial scale. In addition, the flavor of ester exchanged oil can be improved by the present invention.

Next, Examples will further illustrate the present invention.

Example 1

5 g of Lipozyme TL-IM produced by Novozymes A/S was pulverized with a L-type mycolloider produced by Tokushu Kika Kogyo Co., Ltd. When the particle diameters of the pulverized lipase were measured with the particle size distribution analyzer LA-500 produced by HORIBA, Ltd., the average particle diameter was 66.4 μm. 5 g of cellulose powder (Nippon Paper Chemicals Co., Ltd.: the average particle diameter of 30 μm) was added as a filter aid to the powder to prepare a lipase powder composition. The ester exchange activity of this lipase composition was determined by the following method. The result is shown in Table 1 as the relative value thereof.

Measurement Method of Lipase Activity

The lipase composition was added to the oil wherein triolein and tricaprylin were mixed in the ratio of 1:1 (w) and reacted at 60° C. 10 μL thereof was temporally sampled. After diluting it with 1.5 mL of hexane, the lipase composition was filtered, and the filtrate thereof was used as a sample for gas chromatography (GC). The sample was analyzed by GC (column: DB-1ht), and the reaction rate thereof was calculated in accordance with the following formula. The GC conditions are: column temperature: beginning 150° C.; temperature rising: 15° C./min.; and final 370° C.

$$\text{Reaction rate (\%)} = \{C34\text{area}/(C24\text{area} + C34\text{area})\} \times 100$$

wherein, C24 represents tricaprylin; C34 represents tricaprylin wherein one fatty acid is substituted with an oleic acid; and area represents the area dimensions thereof. Based on the reaction rate in each time, the reaction rate constant K was calculated by the analysis software (origin ver. 6.1).

The lipase activity was shown as the relative activity when value K of Lipozyme TL-IM was regarded as 100.

Example 2

5 g of Lipozyme TL-IM produced by Novozymes A/S was pulverized with a mortar. When the particle diameters of the pulverized lipase were measured with the particle size distribution analyzer LA-500 produced by HORIBA, Ltd., the average particle diameter was 52.1 μm. 2.5 g of cellulose powder (Nippon Paper Chemicals Co., Ltd.) was added as a filter aid to the powder to prepare a lipase powder composition. The ester exchange activity of this lipase composition was determined by the same method as that of Example 1. The result is shown in Table 1 as the relative value thereof.

Example 3

50 g of canola oil was added to 5 g of Lipozyme TL-IM produced by Novozymes A/S and pulverized with the homogenizer (Multipro395) produced by DREMEL in 12500 rpm for 3 minutes under cooling with ice. When the particle diameters of the pulverized lipase were measured with the particle size distribution analyzer LA-500 produced by HORIBA, Ltd., the average particle diameter was 91.5 μm. 5 g of cellulose powder (Nippon Paper Chemicals Co., Ltd.) was added as a filter aid thereto and the canola oil was filtered under reduced pressure to obtain a lipase composition. The ester exchange activity of this lipase composition was determined by the same method as that of Example 1. The result is shown in Table 1 as the relative value thereof.

TABLE 1

| | Average particle diameter (μm) | Relative ester exchange activity to the mass of lipase preparation |
|---|---|---|
| Before pulverizing (TL-IM) | 800 | 100 |
| Example 1 | 66.4 | 201 |
| Example 2 | 52.1 | 304 |
| Example 3 | 91.5 | 202 |

Example 4

90 g of canola oil and 10 g of ODO (The Nisshin OilliO Group, Ltd.) were added to 5 g of the lipase composition obtained in Example 1. The mixture was stirred at 25° C. for 5 hours and filtered to collect the lipase composition.

Next, 0.5% of the lipase composition pretreated with the above method was added to 150 g of ODO (The Nisshin OilliO Group, Ltd.) and 850 g of canola oil (The Nisshin OilliO Group, Ltd.) and stirred at 50° C. for 15 hours to conduct the ester exchange reaction. The ester exchange rate was temporally calculated and the proceeding of the reaction was confirmed. Meanwhile, the ester exchange rate was determined by analyzing the glyceride composition with the gas chromatography and calculating the ratio of the ester exchange reactant in the measured sample. FIG. 1 shows changes in the ester exchange rate of the present example and Lipozyme TL-IM (before grinding).

After the reaction, the lipase composition was filtered and collected. The obtained oil was deacidified, decolorized and deodorized by the ordinary methods to purify an ester exchanged oil. The flavor of the obtained ester exchanged oil was evaluated by the trained panelists. As a result, the evaluation thereof was significantly better than that of the ester exchanged oil obtained by the ester exchange using the lipase composition that was not pretreated with canola oil and ODO.

Further, when the collected enzymes were used to conduct the ester exchange reaction, they were able to be recycled 10 times without problems.

Example 5

1 kg of Lipozyme TL-IM produced by Novozymes A/S was pulverized with the pin mill produced by HOSOKAWA-MICRON CORPORATION (Fine Impact Mill 100UPZ) in 17600 rpm. When the particle diameters of the ground lipase were measured with the particle size distribution analyzer LA-500 produced by HORIBA, Ltd., the average particle diameter was 13.8 μm. 1 kg of cellulose powder (Nippon Paper Chemicals Co., Ltd.: the average particle diameter of 30 μm) was added as a filter aid to the powder to prepare a lipase powder composition.

Example 6

90 g of decolorized canola oil and 10 g of ODO (The Nisshin OilliO Group, Ltd.) were added to 5 g of the lipase composition obtained in Example 5. The mixture was stirred at 60° C. for 2 hours and filtered to collect the lipase composition. The ester exchange activity of this lipase composition was determined by the same method as that of Example 1. The result is shown in Table 2 as the relative value thereof.

Example 7

90 g of decolorized canola oil and 10 g of ODO (The Nisshin OilliO Group, Ltd.) were added to 5 g of the lipase composition obtained in Example 5. The mixture was stirred at room temperature for 24 hours and filtered to collect the lipase composition. The ester exchange activity of this lipase composition was determined by the same method as that of Example 1. The result is shown in Table 2 as the relative value thereof.

Example 8

50 g of decolorized canola oil and 50 g of ODO (The Nisshin OilliO Group, Ltd.) were added to 5 g of the lipase composition obtained in Example 5. The mixture was stirred at room temperature for 24 hours and filtered to collect the lipase composition. The ester exchange activity of this lipase composition was determined by the same method as that of Example 1. The result is shown in Table 2 as the relative value thereof.

TABLE 2

| | Relative ester exchange activity to the mass of lipase preparation |
|---|---|
| Before pulverizing (TL-IM) | 100 |
| Example 5 | 474 |
| Example 6 | 557 |
| Example 7 | 714 |
| Example 8 | 600 |

What is claimed is:

1. A purified lipase powder composition which comprises a cellulose filter aid(s) and a product obtained by pulverizing a *Thermomyces* sp.-derived lipase immobilized to a silica carrier(s) wherein the filter aid(s) is/are powdery and has/have an average particle diameter of 10 to 90 μm, wherein the average particle diameter of the resulting pulverized product is 1 to 90 μm, wherein the mass ratio of the pulverized product to the filter aid(s) is 1/7 to 2/1, wherein such purification occurs by contacting at least one long chain fatty acid triglyceride having 14 to 24 carbon atoms in a constituent fatty acid and at least one medium chain triglyceride having 6 to 12 carbon atoms in a constituent fatty acid, and wherein said purified lipase powder composition has improved lipase activity relative to lipase powder compositions that have not been purified using said long chain fatty acid triglyceride and said medium chain triglyceride.

2. The composition according to claim 1, which is used for ester exchange or esterification.

3. A method for exchanging esters of fats and oils which comprises the steps of:
  (1) conducting the ester exchange reaction of the fats and oils in the presence of a purified lipase powder composition which comprises a cellulose filter aid(s) and a product obtained by pulverizing a *Thermomyces* sp.-derived lipase immobilized to a silica carrier(s) wherein the filter aid(s) is/are powdery and has/have an average particle diameter of 10 to 90 μm, wherein the average particle diameter of the resulting pulverized product is 1 to 90 μm, wherein the mass ratio of the pulverized product to the filter aid(s) is 1/7 to 2/1, wherein such purification occurs by contacting at least one long chain fatty acid triglyceride having 14 to 24 carbon atoms in a constituent fatty acid and at least one medium chain triglyceride having 6 to 12 carbon atoms in a constituent fatty acid, and wherein said purified lipase powder composition has improved lipase activity relative to lipase powder compositions that have not been purified using said long chain fatty acid triglyceride and said medium chain triglyceride; and then (2) collecting the lipase powder composition and recycling them.

* * * * *